United States Patent
Pekar et al.

(10) Patent No.: US 8,554,573 B2
(45) Date of Patent: Oct. 8, 2013

(54) INTERACTIVE ATLAS TO IMAGE REGISTRATION

(75) Inventors: Vladimir Pekar, Toronto (CA);
Torbjoern Vik, Hamburg (DE);
Heinrich Schulz, Hamburg (DE); David Jaffray, Etobicoke (CA)

(73) Assignee: Koninklijke Philips N.V., Eindhoven (NL)

( * ) Notice: Subject to any disclaimer, the term of this patent is extended or adjusted under 35 U.S.C. 154(b) by 419 days.

(21) Appl. No.: 12/670,541

(22) PCT Filed: Jul. 11, 2008

(86) PCT No.: PCT/IB2008/052812
§ 371 (c)(1),
(2), (4) Date: Jul. 19, 2010

(87) PCT Pub. No.: WO2009/016530
PCT Pub. Date: Feb. 5, 2009

(65) Prior Publication Data
US 2010/0286995 A1    Nov. 11, 2010

Related U.S. Application Data

(60) Provisional application No. 60/952,257, filed on Jul. 27, 2007.

(51) Int. Cl.
*G06Q 10/00* (2012.01)
(52) U.S. Cl.
USPC .................................. 705/2; 705/3
(58) Field of Classification Search
USPC .......................................................... 705/2
See application file for complete search history.

(56) References Cited

U.S. PATENT DOCUMENTS

| 8,019,142 B2* | 9/2011 | Nowinski et al. ............. 382/131 |
| 2004/0249270 A1 | 12/2004 | Kondo et al. |
| 2005/0022158 A1 | 1/2005 | Launay et al. |
| 2005/0238233 A1* | 10/2005 | Mulet Parada et al. ....... 382/199 |
| 2009/0187388 A1* | 7/2009 | Shu et al. .......................... 703/2 |

FOREIGN PATENT DOCUMENTS

| WO | 9924932 A1 | 5/1999 |
| WO | 2005038711 A1 | 4/2005 |
| WO | 2005059831 A1 | 6/2005 |
| WO | 2005078666 A1 | 8/2005 |

OTHER PUBLICATIONS

Ali, W. S. I., et al.; Registering Coronal Histological 2-D Sections of a Rat Brain with Coronal Sections of a 3-D Brain Atlas Using Geometric Curve Invariants and B-Spline Representation; 1998; IEEE Trans. on Medical Imaging; 17(6) 957-967.

(Continued)

*Primary Examiner* — Hiep V Nguyen

(57) ABSTRACT

When modeling anatomical structures in a patient for diagnosis or therapeutic planning, an atlas (26) of predesigned anatomical structure models can be accessed, and model of one or more such structures can be selected and overlaid on an a 3D image of corresponding structure(s) in a clinic image of a patient. A user can click and drag a cursor on the model to deform the model to align with the clinical image. Additionally, a processor (16) can generate a volumetric deformation function using splines, parametric techniques, or the like, and can deform the model to fit the image in real time, in response to user manipulation of the model.

24 Claims, 5 Drawing Sheets

(56) References Cited

OTHER PUBLICATIONS

Kaus, M. R., et al.; Automated 3D and 4D Organ Delineation for Radiation Therapy Planning in the Pelvic Area; 2004; Medical Imaging; Image Processing; Proc. of SPIE vol. 5370; pp. 346-357.

Schulz, H., et al.; Real-Time Interactive Viewing of 4D Kinematic MR Joint Studies; 2005; Medical Image Computing and Computer-Assisted Intervention; vol. 3749; pp. 467-473.

Toga, A. W., et al.; Image Registration and the Construction of Multidimensional Brain Atlases; 2000; Handbook of Medical Imaging; Elsevier; pp. 635-654.

* cited by examiner

INTERACTIVE ATLAS TO IMAGE REGISTRATION

CROSS REFERENCE TO RELATED APPLICATIONS

This application claims the benefit of U.S. provisional application Ser. No. 60/952,257 filed Jul. 27, 2007, which is incorporated herein by reference.

The present application finds particular utility in medical imaging systems. However, it will be appreciated that the described technique(s) may also find application in other types of imaging systems, scanning systems, and/or other medical applications.

A need for effective interactive tools that allow easy initialization and refinement of a 3-D anatomical atlas is present in many applications. One particular application is in radiotherapy planning. Another application is in the refinement of the result of an automatic segmentation algorithm, since automatic algorithms are often error-prone due to a number of reasons: image artifacts, pathologies, etc.

With conventional techniques, when a user is fitting an outline of an organ to an image of a patient's actual organ, planar slices through the organ are displayed. For instance, three orthogonal slices may be displayed. In current systems, the user can only modify the contours in the slice. This is labor-intensive for volumetric modifications. For 3D surface interaction on the other hand, changes in the slice causes changes in adjacent slices which cannot be seen. This is non-intuitive and requires a high level of expertise when using conventional systems. Finally, for surface mesh representations, the mesh can degenerate when much user-interaction is performed.

There is an unmet need in the art for systems and methods that facilitate overcoming the deficiencies noted above.

In accordance with one aspect, a system for interactive registration of an anatomical structure model to a 3D clinical image include a memory that stores an atlas of 3D contoured models of anatomical structures; a display that presents a view of a patient image and a selected contoured model overlaying the patient image, and a user input device that a user employs to move one of a selected pair of landmark points on the model. The system further includes a processor that receives landmark point movement information from the user input device and executes an algorithm for adjusting a display plane of the contoured model in real time.

In accordance with another aspect, a method of interactively registering a 3D contoured anatomical structure model to a clinical image of the structure in a patient includes presenting a model, selected from an atlas of models and overlaid on the clinical image, to a user, and deforming a portion of the selected model in a direction indicated by the user. The method further includes displaying a pair of user-entered landmark points, which define start and end points along the portion of the deformed model, and adding the landmark points to a set of landmark point pairs stored in a memory. The method also includes calculating a volumetric deformation function for the model using the user-entered landmark points, applying the volumetric deformation function to deform the model, and presenting the updated model to the user in substantially real time.

According to another aspect, an elastic 3D contoured model registration apparatus, includes means for presenting a model, selected from an atlas of models and overlaid on the clinical image, to a user, and means for permitting the user to click on the model and drag a cursor in a direction in which the user wants to deform the model. The apparatus further includes means for displaying a pair of user-entered landmark points, which define start and end positions of a line of travel of the cursor, to the user, and means for adding the landmark points to a set of landmark point pairs stored in a memory, calculating a volumetric deformation function for the model using the user-entered landmark points, and applying the volumetric deformation function to deform the model. The means for presenting displays the updated model to the user in real time.

Yet another aspect relates to an atlas of 3D contoured models of anatomical structures, including a plurality of models of anatomical structures, generated from scanned images of anatomical structures of one or more subjects, wherein the models are deformable in three dimensions and in substantially real time by a user. A machine-readable medium stores the plurality of models for recall and manipulation by an operator.

Another aspect relates to a therapy planning method, including inputting patient image data, selecting a contour model, from an atlas of contoured models, based on patient data, to overlay the patient image data, and manipulating the selected contour model to develop a therapy plan.

One advantage is that 3D contoured models of anatomical structures are deformed in real time, mitigating a need for staying within a defined display plane when deforming a model.

Another advantage resides in employing user-entered landmarks to dynamically adjust a display plane.

Still further advantages of the subject innovation will be appreciated by those of ordinary skill in the art upon reading and understand the following detailed description.

Still further advantages are realized in that the method is meshless. It is thus independent of the surface representation, and problems with degenerating meshes are avoided.

The innovation may take form in various components and arrangements of components, and in various steps and arrangements of steps. The drawings are only for purposes of illustrating various aspects and are not to be construed as limiting the invention.

Figure 1:
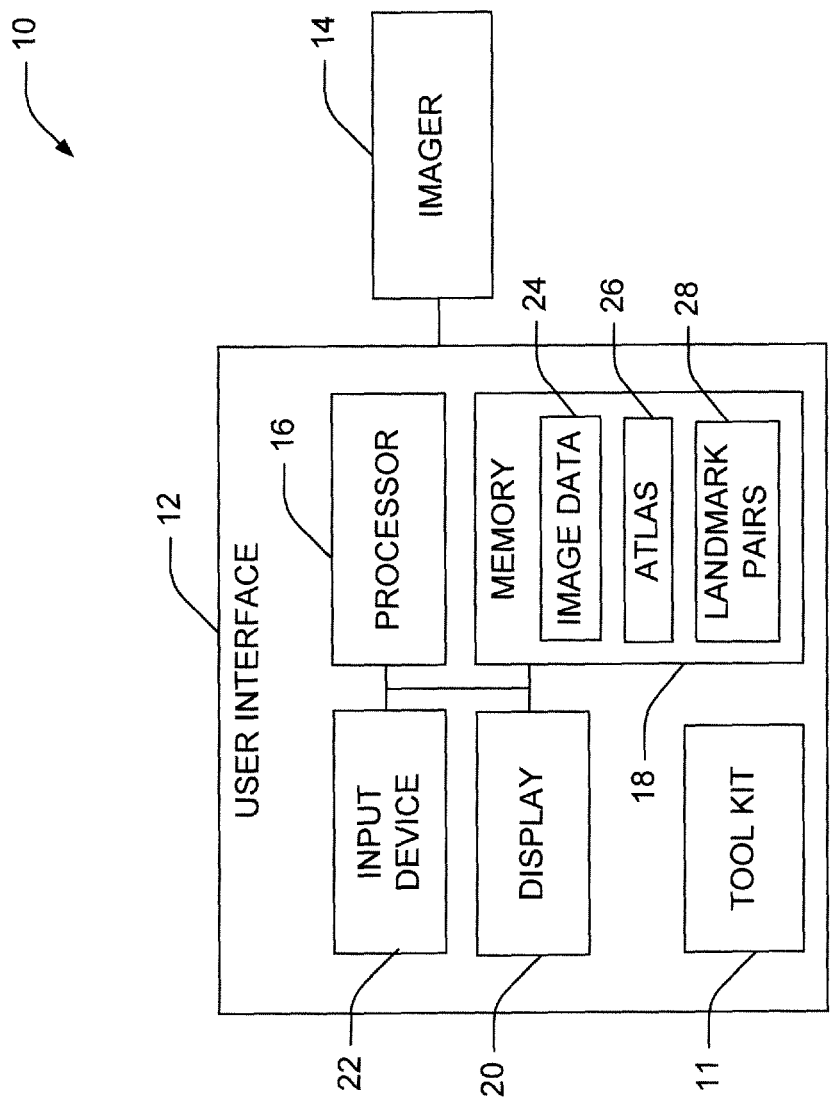
FIG. 1 illustrates a manual editing tool for elastically registering an atlas of anatomical structures to 3D clinical images to provide dynamic display plane updates in real time, in accordance with various aspects.

FIG. 1 illustrates a manual editing tool 10 for elastically registering a contour(s) selected from an atlas 26 of anatomical structures to 3D clinical images. The editing tool provides dynamic display plane updates in real time. The atlas can include models of one or several anatomical structures, (e.g., organs such as the heart lung(s), brain, spleen, liver, intestine, stomach, gall bladder; other structures such as bone(s), muscle, etc.), and such structures can be parameterized. Further, a plurality of models can be provided for various anatomical structures, e.g., corresponding to adult, child, obese, skinny, male, female, etc. For instance, parameterization can be performed using a mesh technique, non-uniform rational B-splines (NURBS), or some other parameterization protocol. The tool 10 facilitates providing a user with a reliable, intuitive, and interactive 3D editing application. According to one embodiment, the tool uses techniques similar to those used in the gaming industry (See, e.g., M. Müller, B. Heidelberger, M. Teschner, and M. Gross. Meshless deformations based on shape matching. *Proc. of SIGGRAPH '05*, pages 471-478, 2005, describing a technique for rendering a surface and not volumetric image information).

The tool 10 facilitates 3D manipulation of a contoured image volume model, which in turn permits a user to manipulate contours of an image volume model in multiple planes, rather than in just one plane. For instance, a user accesses a virtual tool kit 11 with electronically-defined tools to push, pull, or otherwise adjust the model contour in three dimensions. For example, the tools define surfaces of various radii, shapes, and sizes, including a single point, that can press or pull the contour to mold its shape. The user can push or pull the tool along the displayed plane or at an angle to the displayed plane. As a point on the contour is pulled or pushed off of one or more of the displayed planes, the tool automatically changes the displayed plane(s) so that the user can see a desired image volume contour portion superimposed on a diagnostic image volume throughout the period during which the contour portion is being manipulated. The image volume can comprise one or multiple anatomical structures, e.g., adjacent organs. For instance, a user can pull a specific point on a contour or contoured model to a corresponding point on an image of an anatomical structure in a patient. In one example, a significant point may be a spinous process on a vertebra, and the user can drag a corresponding process on the contoured model to the spinous process on the patient's vertebra to more closely align the model to the actual image volume. Between constrained points, the model elastically deforms. Contoured models, which can comprise one or more anatomical structures, are generated from patient data, such as scans or other images of the structure(s). In one embodiment, a number of scans or images of one or more subjects are employed to generate one or more average, or "normal," model(s) of the structure(s).

The displayed slice or surface need not be planar, but may be curved as well. For instance, a contour surface can be curved to match the curvature of a spine. In one embodiment, organ outlines are stored in the atlas individually, and can be combined or assembled by the user to form an area of interest. In another embodiment, outlines for organs in commonly imaged areas can be preassembled, such that the outlines for all organs in preassembled area can be downloaded, uploaded, or otherwise accessed as a group.

The tool includes a user interface 12 that is coupled to an imager 14. For instance, the imager 14 can be a computed tomography (CT) scanning system or a variant thereof, a magnetic resonance imaging (MRI) system or variant thereof, or any other suitable imager for generating 2D or 3D images of a patient or portion of a patient.

The user interface 14 includes a processor 16 that executes machine-readable instructions and/or routines, which are stored in a memory 18, for manipulating a 3D image of one or more organs in a patient. Such images are displayed to a user via a display 20, and the user is permitted to manipulate the images using an input device 22. The memory 18 additionally stores information and/or routines related to the atlas 26, including 3D images and/or maps of various organs, which are then used as a template on which is overlaid a corresponding image 24 of a patient's organ(s). Additionally, the memory stores information and/or routines related displaying patient and atlas images to the user via the display 20, as well as routines for manipulating atlas and/or patient images in response to user input via the input device 22. Moreover, the memory stores image data 24 related to the image of the patient and landmark data 28 describing landmark pairs and the like. The input device can be, for example, a keyboard and cursor, a stylus, a mouse, or some other suitable input device.

Figure 2:
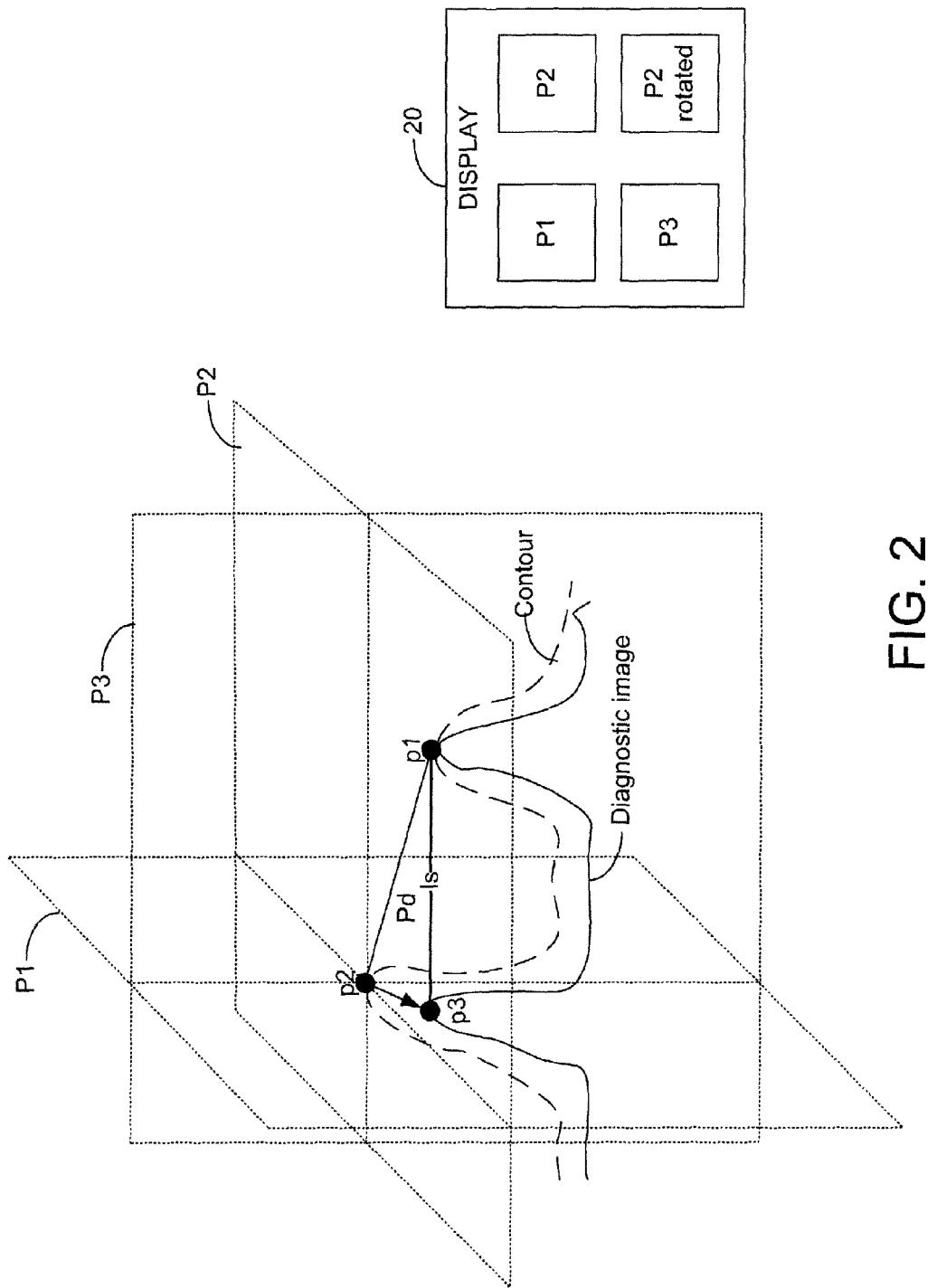
FIG. 2 illustrates a line segment (ls) between two landmark points ($p_1$, $p_2$) that defines a set of planes (e.g., an infinite number of planes that contain the line segment).

FIG. 2, which is to be viewed in conjunction with FIG. 1, illustrates a line segment (ls) between two landmark points $(p_1, p_2)$ that defines a set of planes (e.g., an infinite number of planes that contain the line segment). In an example, a displayed plane $(P_d)$ is a function of the line segment between two landmarks, and a point $p_3$ to which one of the landmarks is moved by the user. For instance, the initial positions of the two landmark points $p_1$ and $p_2$ provide two points to define the display plane $P_d$, and the final position $p_3$ of the manipulated landmark point provides a third point to complete the set of three points to define the display plane. In this example, the user clicks on one of the two landmark points, drags the selected landmark point to new 3D coordinates, and releases the mouse button. The coordinates at which the mouse button is released are registered by the processor 16, and stored to memory 18 as a new landmark pair. In this manner, the new coordinates to which the user moves one of the landmark points are used to define the display plane, and thus the adjusted landmark point is within the display plane and visible to the user. The processor 16 reorients the corresponding one of the displayed slices to lie in the defined display plane $P_d$.

For example, the display 20 displays three orthogonal planes $P_1$, $P_2$, and $P_3$, which intersect at point $p_2$, which is to be moved. As point $p_2$ is moved to point $p_3$, the new display plane $P_d$ is defined, and the corresponding displayed plane $P_2$ is rotated to become co-planar with plane $P_d$.

In another embodiment, the atlas comprises a plurality of labeled models representing different anatomical structures or combinations or structures that may be imaged by the imager 14. Additionally, the atlas can comprise a number of different-sized models for each anatomical structure or combination of structures. For instance, liver-and-kidney models of different sizes can be stored in the atlas as well as separate liver models and kidney models, which may also have multiple sizes. A user can associate first and second points in the model with first and second points in the diagnostic image, and can deform the model to match the diagnostic image. For instance, the user can drag a landmark point to a new location and see how the view changes as the landmark is dragged.

According to another embodiment, a user can zoom in on the image and model for fine-tuning of the contour. Additionally, a user can employ arrow keys or the like, in addition to or in place of, the stylus or mouse to manipulate the landmark points. The processor can employ splines with local and/or global support to facilitate elastic warping of the contoured model(s) to the image. In another embodiment, deformation of the model(s) by the user can be limited by a bounding box or the like, beyond which the user may not drag a landmark point to deform the model or contour thereof.

Figure 3:
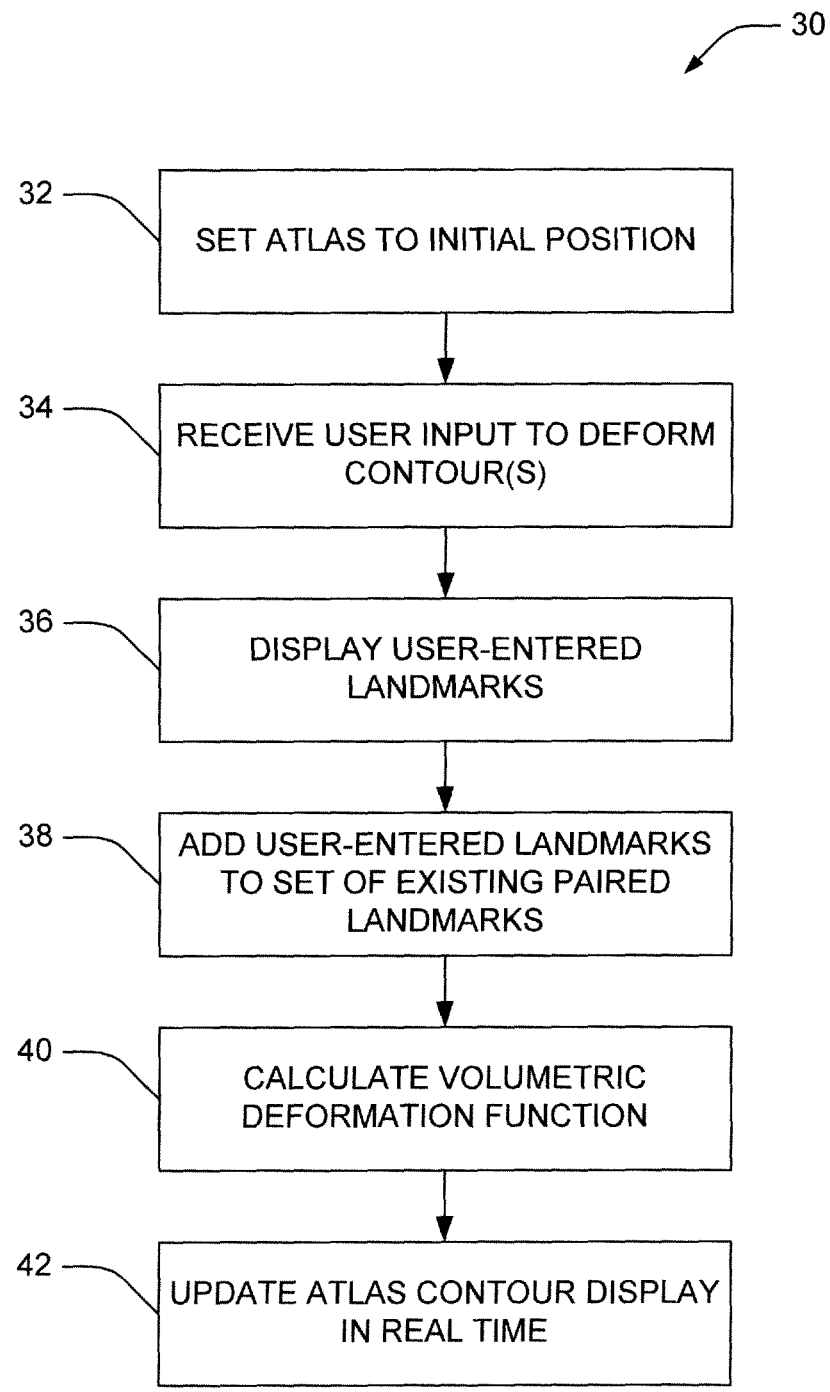
FIG. 3 illustrates a method for manipulating images of anatomical structures in a patient, according to various features described herein.

FIG. 3 illustrates a method 30 for manipulating images of anatomical structures in a patient, according to various features described herein. The method can be, for instance, executed by the processor 16 as a sequence of routines or the like. In one embodiment, the processor and/or a user brings an atlas of anatomical structures to an initial position (e.g., either automatically or manually, respectively), at 32. For example, planar, orthogonal slices of an image, generated by the imager 14, are displayed together with the contours of the surface models (e.g., from the atlas) intersecting the planar slices. In order to improve the initial segmentation, the user employs a mouse or stylus to click and draw, in any chosen plane, in the direction the user wants to deform the contour. Landmark information is received by the processor and/or memory at 34. When the user releases the mouse or stylus button, a pair of corresponding landmarks is displayed in the image, e.g. connected by a line segment, at 36. The landmarks define the beginning and end points of the segment, and are added to a set (which may be empty initially) of already existing paired landmarks stored in the memory, at 38.

From the set of paired landmarks, a volumetric deformation function is calculated (e.g. by using mass-spring models, or parametric transformations such as based on Wendland functions, elastic body splines, thin-plate splines, etc.) and applied to the atlas, at 40. The display of the atlas contours is updated on the fly (e.g., in real time) when a new landmark pair is inserted to or deleted from the set, at 42. In this manner, the user simply clicks and drags points on a patient's image to more closely align the image with the stored atlas image(s) in a selected plane.

Figure 4:
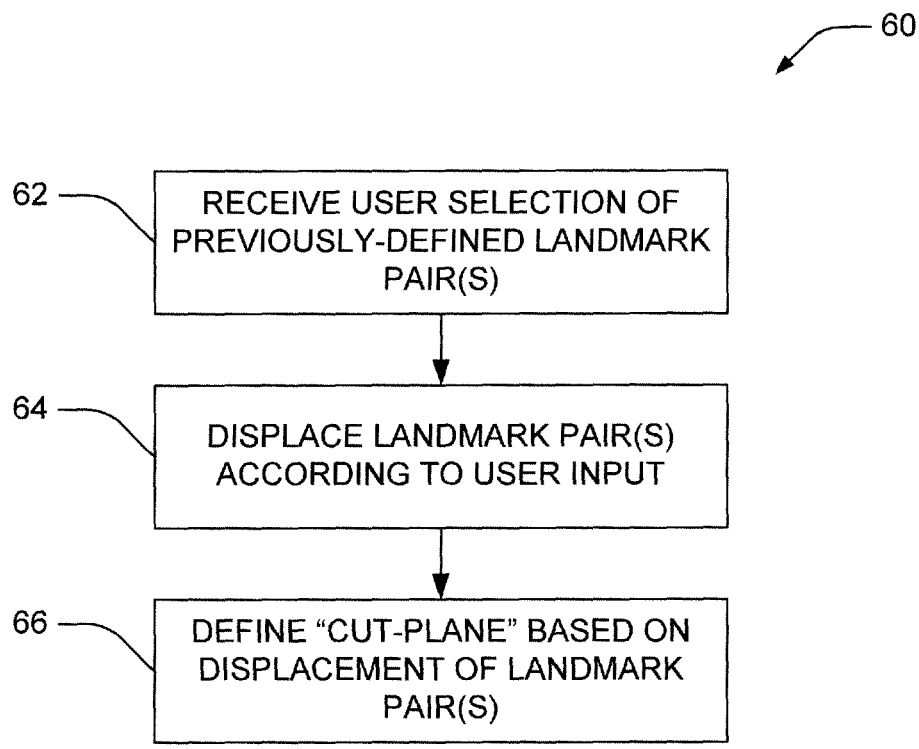
FIG. 4 is an illustration of a method of generating slice views of an image volume, in accordance with various features.

FIG. 4 is an illustration of a method 60 of generating slice views of an image volume, in accordance with various features. The method can be, for instance, executed by the processor 16 as a sequence of routines or the like. A user-defined landmark pair is selected by a user, at 62. The user drags a landmark using the user input device 22, and the processor displaces the landmark on the display 20 according to user input, at 64, to refine the output result. According to one embodiment, the user can jump to any of the landmark pairs and see a slice through the image volume that contains the line segment defined by the two landmarks, e.g. by using an ortho-viewer or the like.

Optionally, the user can adjust the landmark to define a "cut-plane'" which, after releasing the mouse or stylus button, displays a slice that "cuts" the image volume orthogonally to the slice view that was used to adjust the landmark, at 66. Providing the cut-plane can facilitate enhancing 3D interaction.

In other embodiments of the described systems and/or methods, specialized input devices, such as a 3D mouse or joystick, can be used to further improve the efficiency of manual interactions. The described techniques can be used as a pure manual editing tool or to provide pre- and post-processing functionality in combination with any suitable automated registration and segmentation techniques. Additionally, the systems and methods herein can be used in medical image processing systems, therapy planning workstations, and the like, as will be appreciated by those of skill in the art.

Figure 5:
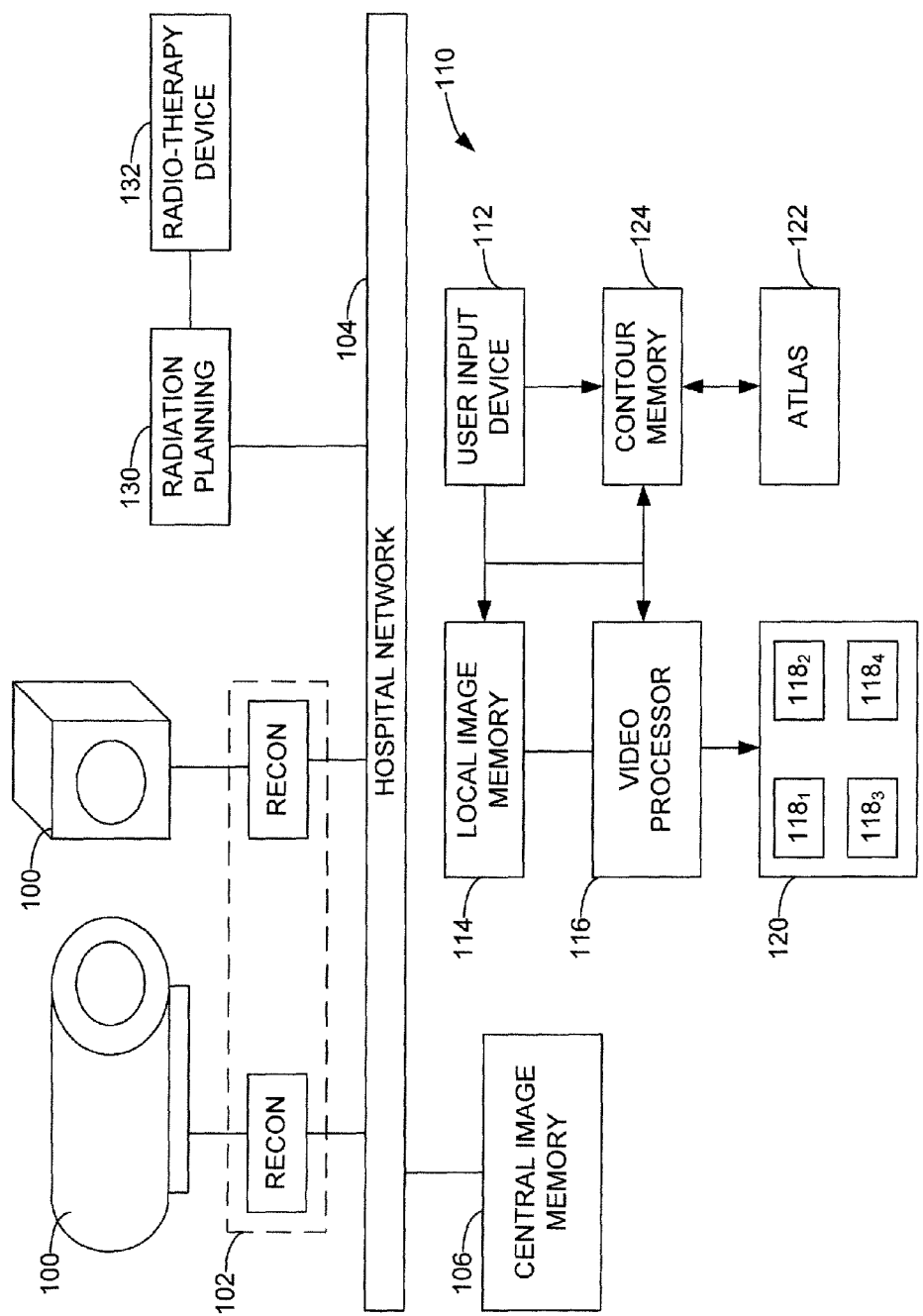
FIG. 5 illustrates a hospital system that may be employed in conjunction with the various systems and/or methods described herein.

With reference to FIG. 5, an exemplary hospital system may include a plurality of imaging devices 100, such as CT, MRI, or the like, which generate imaging data that are reconstructed by individual or shared reconstruction processors 102 to generate 3D image representations. The image representations are communicated over a network 104 to a central memory 106.

At a station 110 connected with the network, an operator uses an input device 112 to move a selected 3D image representation from the central memory to a local memory 114. A video processor 116 selects, for example, three orthogonal slices, which are displayed in view ports $118_1$, $118_2$, and $118_3$ of a monitor 120. A fourth view port $118_4$ can display a surface rendered volume, close-up view, or the like. The operator, trough the input device 112, selects the slices to be displayed.

The operator uses the input device to select a 3D contour from an atlas 122 that can be stored in a selected contour memory 124. The video processor superimposes the same three planes of the selected contour on the slices displayed in ports $118_1$, $118_2$, and $118_3$. To conform the contour to the shape of one or more of the organs in the diagnostic image, the operator uses the input device to designate the characteristic points on one or more of the 3D slices. As described above, the operator can designate a first characteristic point, e.g., a characteristic point of the image and the contour that have already been brought into coincidence. The operator then designates a second characteristic point on the image and a third characteristic point on the contour, which third characteristic point on the corresponds to the second characteristic point. Note that these three points may not be visible concurrently. Rather, the operator may have to shift one or more of the displayed planes to find and/or designate the three characteristic points.

Once the three points have been designated, the video processor display a slice defined by the three points, e.g., in the fourth view port $118_4$. As the operator pulls or pushes the third characteristic point on the contour toward the second characteristic point on the organ, the contour deflects elastically in three dimensions. During this motion, the operator can watch the deflection of the contour in the plane of the motion on the fourth view port. Changes in the contour may also be seen in the other displayed slices. The changed contour shape is stored in the memory 124. The operator repeats this procedure as many times as necessary to conform the contour to the organ.

The shaped contour can be stored in the central memory 106 or used directly in another process. For instance, a therapy planning (e.g., radiation, ablation, etc.) station 130 can use the contour to plan a therapy session. Once planned to the satisfaction of the operator, the planned therapy is transferred to a therapy device 132 that implements the planned session. Other stations may use the shaped contour in various other planning processes.

Having thus described the preferred embodiments, the invention is now claimed to be:

1. A system for interactive registration of an anatomical structure model to a 3D clinical image, including:
    a memory that stores an atlas of 3D contoured models of anatomical structures;
    a display that presents a view of a patient image and a selected contoured model overlaying the patient image;
    a user input device that a user employs to move one of a selected pair of landmark points on the model to a third landmark point; and
    a processor that receives landmark point movement information from the user input device and executes an algorithm for adjusting a display plane of the contoured model in real time, wherein the display plane is defined by the selected pair of landmark points and the third landmark point.

2. The system according to claim 1, wherein the atlas includes differently-sized contoured models of a given anatomical structure.

3. The system according to claim 2, wherein the atlas includes contoured models of groups of anatomical structures.

4. The system according to claim 1, wherein the input device includes a button that the user depresses while hovering a cursor at a first location on the displayed contoured model, moves the cursor to a second location on the displayed contour model, and releases the button at the second location to define a line segment.

5. The system according to claim 4, wherein the first and second locations are stored to the memory as a pair of landmark points.

6. The system according to claim 5, wherein the user selects a pair of landmark points and drags a first landmark point of the pair of landmark points to a new position to define the display plane, and the processor updates the display plane in real time as the user drags the first landmark point.

7. The system according to claim 1, wherein the user selects first and second landmark points on the diagnostic image and the third landmark point on the contoured model, which third landmark point corresponds to one of the first and second landmark points and wherein the algorithm executed by the processor defines a slice in the plane defined by the first, second, and third landmark points and causes the display to display the slice.

8. The system according to claim 1, wherein the contoured model is deformed to align with the clinical image and a radiation therapy plan is generated using the deformed contoured model.

9. The system according to claim 1, wherein the processor generates a volumetric deformation function and applies the function to the contoured model to adjust the display plane.

10. The system according to claim 9, wherein the processor generates the volumetric deformation function using at least one of a spring-mass model, Wendland-function parametric transformation, elastic-body splines, or thin-plate splines.

11. The system according to claim 1, wherein the 3D contoured models are generated from patient image data.

12. The system according to claim 1, further including:
a routine for setting the contoured model to an initial position overlaying an image of a patient;
a routine for receiving user input to deform the contoured model;
a routine for displaying user-entered landmark points;
a routine for adding user-entered landmark point pairs to a set of existing landmark point pairs;
a routine for calculating a volumetric deformation function for deforming the contoured model according to the user input; and
a routine for updating a displayed contour of the model in real time.

13. The system according to claim 1, wherein the processor is configured to:
receive user input relating to user-defined landmark point pairs within the displayed contoured model;
update landmark pair coordinates in the contoured model stored in the atlas;
receive user input related to movement of a first landmark point in a selected landmark point pair; and
update the contoured model in real time in response to the movement of the first landmark point.

14. A method for interactively registering the anatomical structure model of claim 1, including:
setting the model to an initial position overlaying an image of an anatomical structure of a patient;
receiving user input to deform a contour of the model;
displaying, on the display, user-entered landmarks on the model;
adding the user-entered landmarks to a set of landmark pairs for the model;
calculating a volumetric deformation function as a function of the position of the user-entered landmarks;
applying the volumetric deformation function to the model; and
updating the model presented on the display in real time for the user.

15. A method of interactively registering a 3D contoured anatomical structure model to a clinical image of the structure in a patient, including:
presenting a model, selected from an atlas of models and overlaid on the clinical image, to a user via a display;
deforming a portion of the selected model in a direction indicated by the user;
displaying a pair of user-entered landmark points, which define start and end points along the portion of the deformed model;
adding the landmark points to a set of landmark point pairs stored in a memory;
calculating a volumetric deformation function for the model using the user-entered landmark points;
applying the volumetric deformation function to deform the model;
presenting the updated model on the display to the user in substantially real time;
receiving information related to a user selection of a pair of corresponding landmark points, one on the model and one on the clinical image;
defining a display plane on which the pair of landmark points lie;
displacing the model landmark point in the selected landmark point pair along the display plane toward the clinical image landmark point;
defining a cut-plane that is orthogonal to a display plane in which the at least one landmark point is displaced; and
presenting the cut-plane view of the model to the user.

16. The method according to claim 15, wherein presenting the updated model includes:
defining a plane that intersects the line of travel and a point on the model that corresponds to a point on the line of travel;
displaying a slice image through the defined plane;
and dragging the point on the model along the defined plane to deform the model.

17. The method according to claim 15, further including generating a therapy plan using the updated model.

18. The method according to claim 15, wherein the volumetric deformation function is generated using at least one of a spring-mass model, Wendland-function parametric transformation, elastic-body splines, or thin-plate splines.

19. The method according to claim 15, wherein the input device is at least one of a mouse or a stylus.

20. The method according to claim 15, wherein the atlas includes at least one of a plurality of models of different anatomical structures, different sized models of a one or more anatomical structure, and models of one or more different combinations of anatomical structures.

21. A processor or non-transitory computer-readable medium programmed to:
present a model, selected from an atlas of models and overlaid on the clinical image, to a user via a display;
deform a portion of the selected model in a direction indicated by the user;
display a pair of user-entered landmark points, which define start and end points along the portion of the deformed model;
add the landmark points to a set of landmark point pairs stored in a memory;
calculate a volumetric deformation function for the model using the user-entered landmark points;
apply the volumetric deformation function to deform the model;
present the updated model on the display to the user in substantially real time;
receive information related to a user selection of a pair of corresponding landmark points, one on the model and one on the clinical image;

define a display plane on which the pair of landmark points lie;

displace the model landmark point in the selected landmark point pair along the display plane toward the clinical image landmark point;

define a cut-plane that is orthogonal to a display plane in which the at least one landmark point is displaced; and present the cut-plane view of the model to the user.

22. An elastic 3D contoured model registration apparatus, including:

a display that presents a model, selected from an atlas of models and overlaid on the clinical image, to a user;

an input device that permits the user to click on the model and drag a cursor in a direction in which the user wants to deform the model;

wherein the display displays a pair of user-entered landmark points, which define start and end positions of a line of travel of the cursor, to the user;

a processor that adds the landmark points to a set of landmark point pairs stored in a memory, calculates a volumetric deformation function for the model using the user-entered landmark points, and applies the volumetric deformation function to deform the model;

wherein the display displays the updated model to the user in real time;

wherein the processor:

receives information related to a user selection of a pair of corresponding landmark points, one on the model and one on the clinical image;

defines a display plane on which the pair of landmark points lie;

displaces the model landmark point in the selected landmark point pair along the display plane toward the clinical image landmark point;

defines a cut-plane that is orthogonal to a display plane in which the at least one landmark point is displaced; and wherein the display presents the cut-plane view of the model to the user.

23. An atlas of 3D contoured models of anatomical structures, including:

a plurality of models of anatomical structures, generated from scanned images of anatomical structures of one or more subjects, wherein the models are deformable in three dimensions and in substantially real time by a user; and a non-transitory machine-readable medium that stores the plurality of models for recall and manipulation by an operator;

wherein the models are deformable via a user input device that a user employs to move one of a selected pair of landmark points on the model to a third landmark point, and wherein a display plane is defined by the selected pair of landmark points and the third landmark point.

24. A therapy planning method, including:

inputting patient image data;

selecting a contoured model, from an atlas of contoured models displayed to the user on a display, based on patient data, to overlay the patient image data; and manipulating the selected contoured model to develop a therapy plan;

wherein the contoured model is manipulated via a user input device that a user employs to move one of a selected pair of landmark points on the model to a third landmark point, and wherein a display plane is defined, by a processor, by the selected pair of landmark points and the third landmark point.

* * * * *